United States Patent [19]

Vandenberk et al.

[11] Patent Number: 5,196,425

[45] Date of Patent: Mar. 23, 1993

[54] ANTIHYPERTENSIVE 3-PIPERIDINYL-INDAZOLE DERIVATIVES

[75] Inventors: Jan Vandenberk, Beerse; Ludo E. J. Kennis, Turnhout; Albertus H. M. T. Van Heertum, Beerse, all of Belgium

[73] Assignee: Janssen Pharmaceutica N.V., Beerse, Belgium

[21] Appl. No.: 380,958

[22] Filed: Jul. 17, 1989

Related U.S. Application Data

[63] Continuation-in-part of Ser. No. 239,915, Sep. 2, 1988, abandoned.

[51] Int. Cl.⁵ .................. C07D 239/72; A61K 31/505
[52] U.S. Cl. .................... 514/258; 514/259; 544/278; 544/282; 544/285; 544/287
[58] Field of Search .............. 544/278, 282, 285, 287; 514/258, 259

[56] References Cited

U.S. PATENT DOCUMENTS

| | | | |
|---|---|---|---|
| 4,665,075 | 5/1987 | Vandenberk et al. | 514/259 |
| 4,670,447 | 6/1987 | Strupczewski | 514/322 |
| 4,710,573 | 12/1987 | Strupczewski | 546/199 |
| 4,758,668 | 7/1988 | Strupczewski | 546/199 |
| 4,775,761 | 10/1988 | Strupczewski | 546/199 |
| 4,804,663 | 2/1989 | Kennis et al. | 514/258 |
| 4,806,649 | 2/1989 | Strupczewski | 546/193 |
| 5,015,740 | 5/1991 | Kennis et al. | 544/284 |

FOREIGN PATENT DOCUMENTS 0196132  3/1986  Belgium .
0135781  8/1984  Fed. Rep. of Germany .

OTHER PUBLICATIONS

J. Med Chem. 1985, 28, 761-769.

*Primary Examiner*—Nicholas S. Rizzo
*Attorney, Agent, or Firm*—Charles J. Metz

[57] ABSTRACT

3-Piperidinyl-indazole derivatives and their pharmaceutically acceptable acid addition salts being useful antagonists of neurotransmitters; pharmaceutical compositions containing the same and a method of treating warm-blooded animals suffering from diseases associated with the release of said neurotransmitters.

6 Claims, No Drawings

ANTIHYPERTENSIVE 3-PIPERIDINYL-INDAZOLE DERIVATIVES

CROSS-REFERENCE TO RELATED APPLICATION

This is a continuation-in-part of our copending application Ser. No. 239,915, filed Sep. 2, 1988, now abandoned.

BACKGROUND OF THE INVENTION

A number of 3-piperidinyl-1,2-benzisoxazoles and 3-piperidinyl-1,2-benzisothiazoles having antiserotonin and antipsychotic activity are known from U.S. patent application No. 4,804,663 and J. Med. Chem. 1985, 28, 761-769. In EP-A-0,135,781, published Apr. 3, 1985, there are disclosed a number of 3-piperidinyl-indazole derivatives as antipsychotics and analgesics.

DESCRIPTION OF THE INVENTION

The present invention is concerned with novel 3-piperidinyl-indazole derivatives having the formula

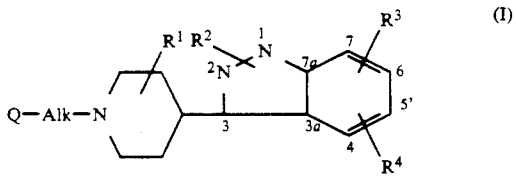

the pharmaceutically acceptable acid addition salts and stereochemically isomeric forms thereof, wherein $R^1$ is hydrogen or $C_{1-6}$alkyl;

$R^2$ is hydrogen; $C_{1-6}$alkyl; hydroxy$C_{1-6}$alkyl; phenyl optionally substituted with up to three substituents independently selected from $C_{1-6}$alkyl, $C_{1-6}$alkyloxy, hydroxy, halo, amino, nitro and trifluoromethyl; aryl$C_{1-6}$alkyl; $C_{1-6}$alkylcarbonyl; $C_{1-6}$alkyloxycarbonyl or phenylcarbonyl, wherein phenyl is optionally substituted with up to three substituents independently selected from $C_{1-6}$alkyl, $C_{1-6}$alkyloxy, hydroxy, halo, amino, nitro and trifluoromethyl;

$R^3$ and $R^4$ each independently are hydrogen, halo, hydroxy, $C_{1-6}$alkyloxy or $C_{1-6}$alkyl;

Alk is $C_{1-4}$alkanediyl; and

Q is a bicyclic heterocyclic radical of formula

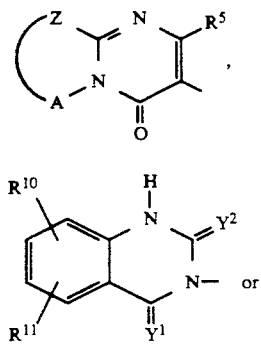

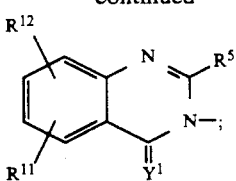

wherein $R^5$ is hydrogen or $C_{1-6}$alkyl;

Z is —S— or —CR$^6$=CR$^7$—; said $R^6$ and $R^7$ each independently being hydrogen or $C_{1-6}$alkyl; or Z is —CH$_2$— wherein one hydrogen atom may be replaced by hydroxy or $C_{1-6}$alkyl;

A is a bivalent radical —CH$_2$—CH$_2$— or —CH$_2$—CH$_2$—CH$_2$— wherein in the latter two radicals one or two hydrogen atoms may be replaced by $C_{1-6}$alkyl; or A is a bivalent radical —CR$^8$=CR$^9$—, wherein $R^8$ and $R^9$ each independently are hydrogen, halo, amino or $C_{1-6}$alkyl; or when Z is —S—, then A may also be —CR$^{10}$=N—, $R^{10}$ being hydrogen or $C_{1-6}$alkyl; or when Z is —CR$^6$=CR$^7$—, then A also may be —O—; and $Y^1$ and $Y^2$ each independently are O or S;

$R^{11}$ is hydrogen, halo, $C_{1-6}$alkyl, $C_{1-6}$alkyloxy, trifluoromethyl, nitro, amino, mono- or di($C_{1-6}$alkyl)amino, $C_{1-10}$alkylcarbonylamino, cyano, hydroxy, $C_{1-10}$alkylcarbonyloxy, phenylmethoxy or azido;

$R^{12}$ is hydrogen or halo; and aryl is phenyl optionally substituted with up to three substituents independently selected from $C_{1-6}$alkyl, $C_{1-6}$alkyloxy, hydroxy, halo, amino, nitro and trifluoromethyl; pyridinyl, furanyl or $C_{1-6}$alkyl substituted furanyl.

In formula (I) the dotted lines within the indazole moiety represent a conjugated diene system, its precise location depending upon the position of the $R^2$ radical: when said $R^2$ is substituted on $N^1$, then the double bonds are located between $N^2$ and position 3 and between positions 3a and 7a of the indazole system; if on the other hand, $R^2$ is substituted on $N^2$, then the double bonds are located between positions 3 and 3a and between positions 7a and $N^1$ of the indazole system.

In the foregoing definitions the term halo is generic to fluoro, chloro, bromo and iodo; $C_{1-6}$alkyl defines straight and branch chained saturated hydrocarbon radicals, having from 1 to 6 carbon atoms, such as, for example, methyl, ethyl, propyl, 1-methylethyl, butyl, 1-methylpropyl, 2-methylpropyl, 1,1-dimethylethyl, pentyl, hexyl and the like; $C_{1-10}$alkyl defines $C_{1-6}$alkyl radicals as defined hereinabove and the higher homologs thereof having from 7 to 10 carbon atoms; $C_{1-4}$alkanediyl defines bivalent straight or branch chained hydrocarbon radicals having from 1 to 4 carbon atoms, such as, for example, methylene, 1,2-ethanediyl, 1,3-propanediyl, 1,4-butanediyl and the branched isomers thereof.

The moiety Z-A in the radical of formula (b) in particular may be —S—CH$_2$—CH$_2$—, —S—CH$_2$—CH$_2$—CH$_2$—, —S—CH=C(CH$_3$)—, —S—C(CH$_3$)=N—, —CH=CH—CH=CH—, —C(CH$_3$)=CH—CH=CH—, —CH=CH—C(CH$_3$)=CH—, —CH=CH—CCl=CH—, —CH=CH—CBr=CH—, —CH=C(CH$_3$)—O—, —CH$_2$—CH$_2$—CH$_2$—CH$_2$—, —CHOH—CH$_2$—CH$_2$—CH$_2$—, —CH(CH$_3$)—CH$_2$—CH$_2$—CH$_2$—, —CH$_2$—CH(CH$_3$)—CH$_2$—CH$_2$— or —CH(CH$_3$)—CH$_2$—CH(CH$_3$)—CH$_2$—.

Depending on the nature of the various substituents the compounds of formula (I) may have several asymmetric carbon atoms. Unless otherwise mentioned or indicated, the chemical designation of compounds denotes the mixture of all possible stereochemically isomeric forms, said mixtures containing all diastereomers and enantiomers of the basic molecular structure. The absolute configuration of each chiral center may be indicated by the stereochemical descriptors R and S, this R and S notation corresponding to the rules described in Pure Appl. Chem. 1976, 45, 11-30. Stereochemically isomeric forms of the compounds of formula (I) are obviously intended to be embraced within the scope of the invention.

Pure stereochemically isomeric forms of the compounds of formula (I) may be obtained by the application of art-known procedures. Diastereoisomers may be separated by physical separation methods such as selective crystallization and chromatographic techniques, e.g., counter current distribution, liquid chromatography and the like; and enantiomers may be separated from each other by the selective crystallization of their diastereomeric salts with optically active acids. Pure stereochemically isomeric forms may also be derived from the corresponding pure stereochemically isomeric forms of the appropriate starting materials, provided that the reaction occurs stereospecifically.

Preferred compounds within the present invention are those compounds of formula (I) wherein $R^1$ is hydrogen; and/or $R^2$ is substituted on $N^1$, and/or $R^3$ and $R^4$ each independently are hydrogen, $C_{1-6}$alkyloxy or halo; and/or Q is a radical of formula (a) wherein $R^5$ is $C_{1-6}$alkyl.

Particularly preferred compounds are those preferred compounds wherein $R^2$ is hydrogen, $C_{1-6}$alkyl, phenyl optionally substituted with halo or trifluoromethyl, or phenylmethyl optionally substituted with halo, $C_{1-6}$alkyloxy or trifluoromethyl; and/or $R^3$ is halo; and/or $R^4$ is hydrogen.

The most preferred compounds are those particularly preferred compounds wherein $R^3$ is 6-fluoro.

The compounds of formula (I) can generally be prepared by N-alkylating an appropriately substituted piperidine of formula (III) with an alkylating agent of formula (II).

Q—Alk—W +

(II)

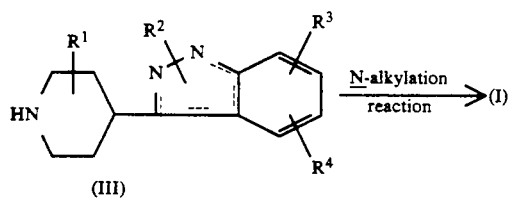

(III)

In formula (II) and in any formula hereinafter wherein it occurs, W represents a reactive leaving group such as, for example, halo, e.g. chloro, bromo or iodo, or a sulfonyloxy group, e.g. methanesulfonyloxy, benzenesulfonyloxy, 4-methylbenzenesulfonyloxy and the like.

The reaction of (II) with (III) can conveniently be conducted in a reaction-inert solvent such as, for example, an aromatic hydrocarbon, e.g., benzene, methylbenzene, dimethylbenzene, and the like; a lower alkanol, e.g., methanol, ethanol, 1-butanol and the like; a ketone, e.g., 2-propanone, 4-methyl-2-pentanone and the like; an ether, 1,4-dioxane, 1,1'-oxybisethane, tetrahydrofuran and the like; N,N-dimethylformamide; N,N-dimethylacetamide; nitrobenzene; 1,3-dimethyl-3,4,5,6-tetrahydro-2(1H)pyrimidinone; 1,3-dimethyl-2-imidazolidinone; 1-methyl-2-pyrrolidinone; and the like. The addition of an appropriate base such as, for example, an alkali or an earth alkaline metal carbonate, hydrogen carbonate, hydroxide, alkoxide or hydride, e.g., sodium carbonate, sodium hydrogen carbonate, potassium carbonate, sodium hydroxide, sodium methoxide, sodium hydride and the like, or an organic base such as, for example, a tertiary amine, e.g., N,N-dimethylethanamine, N-(1-methyl-ethyl)-2-propanamine, 4-ethylmorpholine and the like may be utilized to pick up the acid which is liberated during the course of the reaction. In some circumstances the addition of a iodide salt, preferably an alkali metal iodide, is appropriate. Somewhat elevated temperatures may enhance the rate of the reaction.

The compounds of formula (I) wherein $R^2$ is other than hydrogen, said $R^2$ being represented by $R^{2-a}$, and said compounds by formula (I-a), can be obtained by N-alkylating or N-acylating a 3-piperidinyl-indazole of formula (I-b) wherein $R^2$ is hydrogen, with an alkylating or acylating reagent $R^{2-a}$-$W^1$ (IV).

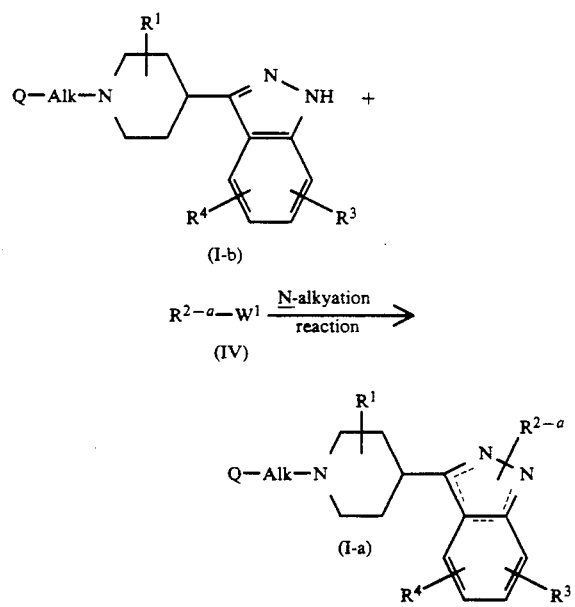

In the reagent of formula (IV) $W^1$ represents an appropriate leaving group such as halo, e.g. chloro, bromo and the like; or a sulfonyloxy group, e.g. methanesulfonyloxy, 4-methylbenzenesulfonyloxy and the like; in the instances wherein $R^{2-a}$ is $C_{1-6}$alkylcarbonyl or optionally substituted phenylcarbonyl $W^1$ may also represent respectively $C_{1-6}$alkylcarbonyloxy or optionally substituted phenylcarbonyloxy (i.e. $R^{2-a}$-$W^1$ is an acid anhydride). Said N-alkylation reaction of (I-b) with a reagent (IV) may be carried out by stirring and, if desired, heating the reactants, optionally in an appropriate reaction-inert solvent such as, for example, an aromatic hydrocarbon, e.g., benzene, methylbenzene, dimethylbenzene, and the like; a lower alkanol, e.g., methanol, ethanol, 1-butanol and the like; a ketone, e.g., 2-propanone, 4-methyl-2-pentanone and the like; an ether, 1,4- dioxane, 1,1'-oxybisethane, tetrahydrofuran and the like; a dipolar aprotic solvent, e.g. N,N-dimethylformamide, N,N-dimethylacetamide, nitrobenzene, 1,3-dimethyl-3,4,5,6-tetrahydro-2(1H)-pyrimidinone, 1,3-dimethyl-2-imidazolidinone, 1-methyl-2-pyrrolidinone and the like. Further the addition of a base such as, for example, aqueous alkali, e.g. sodium or potassium hydroxide, sodium or potassium carbonate and the like; or an alkali metal alkoxide such as, for example, sodium methoxide, sodium ethoxide, potassium tert.-butoxide and the like may be appropriate. In case mixtures of 1- and 2-substituted indazoles are obtained, said mixtures may be separated by the application of art-known methods such as, for example, selective crystallization, chromatography and the like.

The compounds of formula (I) may also be prepared by the cyclization reaction of an intermediate of formula (V) with an appropriate hydrazine derivative $R^2-NH-NH_2$ (VI) or an acid addition salt thereof.

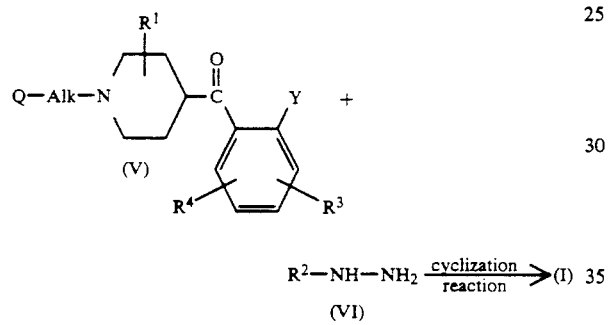

In formula (V) Y represents an appropriate leaving group such as, for example, halo, e.g. fluoro or chloro; or a nitro group. Said cyclization reaction may be conducted by stirring, and if desired, heating the reactants in a suitable reaction-inert solvent in the presence of an appropriate base. Suitable solvents generally have a relatively high boiling point and are, for example, water; alkanols, e.g. methanol, ethanol, 1-butanol and the like; diols, e.g. 1,2-ethanediol and the like; aromatic hydrocarbons, e.g. benzene, methylbenzene, dimethylbenzene and the like; halogenated hydrocarbons, e.g. trichloromethane, tetrachloromethane and the like; ethers, e.g. tetrahydrofuran, 1,4-dioxane, 1,1'-oxybisbutane, 1,1'-oxybis-(2-methoxyethane) and the like; dipolar aprotic solvents, e.g. N,N-dimethyl-formamide, N,N-dimethylacetamide, dimethylsulfoxide and the like; or mixtures of such solvents. Appropriate bases preferably are alkali or earth alkaline metal carbonates or hydrogen carbonates such as, for example, sodium hydrogen carbonate, sodium carbonate, potassium carbonate and the like; or amines such as N,N-diethylethanamine, 4-ethylmorpholine, N-(1-methylethyl)-2-propanamine and the like.

Additionally, the compounds of formula (I) may be prepared by the nitrosation of an intermediate aniline of formula

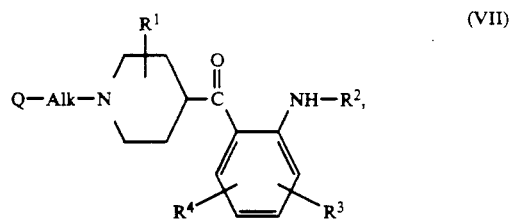

with an alkali metal nitrite, e.g. sodium nitrite, in an aqueous acidic medium and treating the thus obtained N-nitroso compound (VIII-a) or, in case $R^2$ is hydrogen, the diazonium salt (VIII-b),

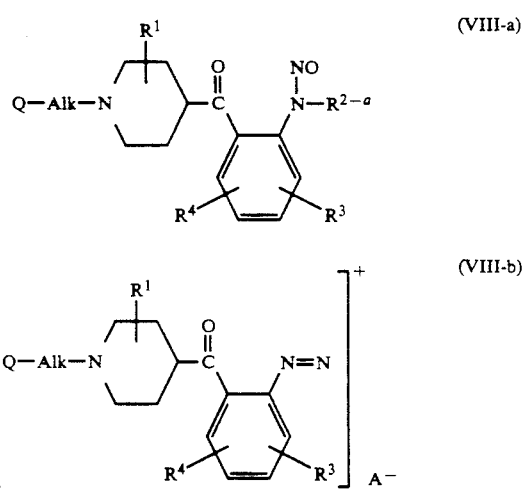

wherein $A^-$ represents the conjugated base of the acid used hereinabove, with an appropriate reducing agent such as, for example, hydrogen in the presence of a hydrogenation metal catalyst, e.g. Raney nickel or Raney cobalt; or a sulfite, e.g. sodium sulfite, thus yielding the corresponding hydrazine derivative of formula

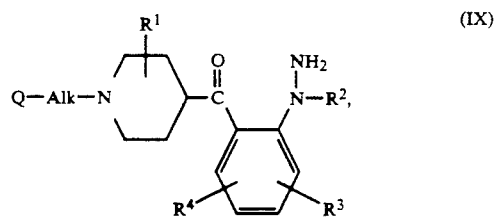

which in most instances spontaneously, or if necessary upon increasing the temperature, may cyclize to a compound of formula (I).

The compounds of formula (I) may also be prepared following art-known procedures n for building up radicals of formula Q. For example, the compounds of formula (I) wherein Q is radical of formula (b), said compounds being represented by formula (I-c), can be obtained from an intermediate of formula (X) by condensation with a reagent of formula (XI), wherein each L independently represents an appropriate leaving group.

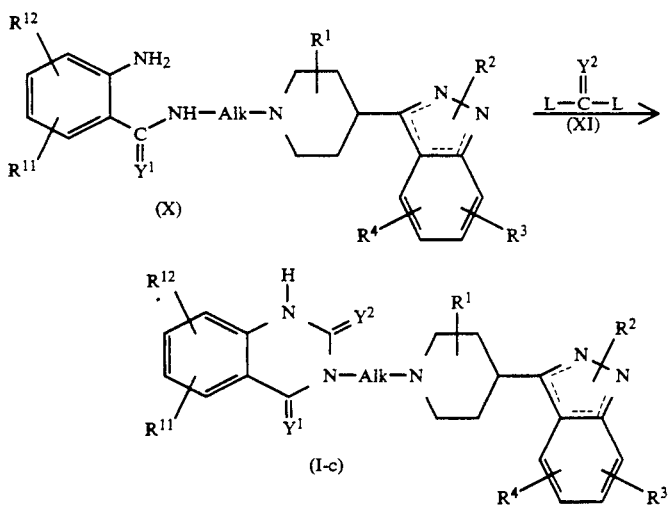

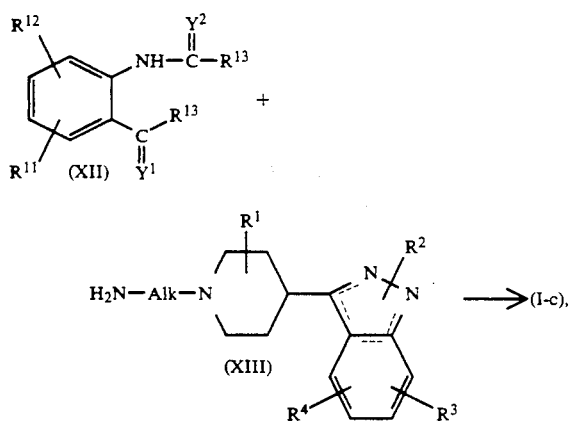

As typical examples of reagents of formula (XI) there may be mentioned urea, thiourea, carbonic dichloride, 1,1'-carbonylbis[1H-imidazole], di($C_{1-6}$alkyl)carbonates such as dimethyl carbonate, diethylcarbonate and the like, chloroformates such methyl chloroformate, ethyl chloroformate, phenyl chloroformate and the like reagents.

The compounds of formula (I-c) can also be prepared by cyclizing an intermediate of formula (XII) with a primary amine of formula (XIII)

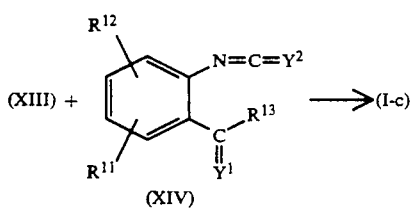

or by cyclizing an isocyanate or isothiocyanate of formula (XIV) with an amine of formula (XIII).

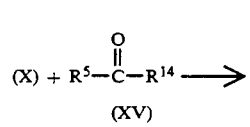

In the foregoing reaction schemes each $R^{13}$ independently represents an appropriate leaving group such as, for example, $C_{1-6}$alkyloxy, amino, mono- or di($C_{1-6}$alkyl)amino; and in formula (XII) both $R^{13}$ groups taken together may also represent -O-. Said cyclization reactions are conveniently conducted by stirring and, if desired, heating the reactants, optionally in a suitable reaction-inert solvent such as an aliphatic or aromatic hydrocarbon, e.g. petroleum ether, dimethylbenzene and the like; a halogenated hydrocarbon, e.g. dichloromethane, trichloromethane, 1,2-dichloroethane and the like; an ether, e.g. tetrahydrofuran, 1,4-dioxane and the like; a ketone, e.g. 2-propanone, 4-methyl-2-pentanone and the like.

The compounds of formula (I) wherein Q is a radical of formula (c), said compounds being represented by formula (I-d), can be obtained by treating an intermediate of formula (X) with a carboxylic acid of formula (XV) or, a suitable functional derivative thereof such as an acyl halide, an an anhydride or an ester. In (XV) and in the formulae hereinafter each $R^{14}$ independently represents an appropriate leaving group such as, for example, hydroxy, halo, $C_{1-6}$alkyloxy, $C_{1-6}$alkylcarbonyloxy, amino, mono- or di-($C_{1-6}$alkyl)amino.

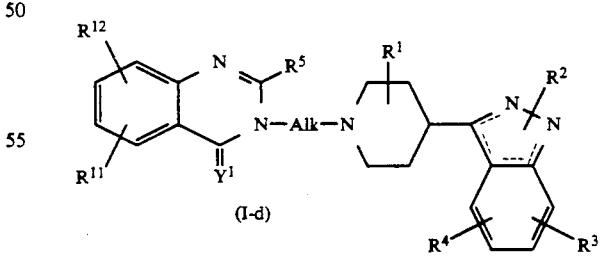

The compounds of formula (I) wherein Q is a radical of formula (a), said compounds being represented by the formula (I-e), can be prepared following art-known cyclization procedures for preparing pyrimidin-4-ones such as, for example, by reacting an amine of formula (XVI) with a β-dicarbonyl compound of formula (XVII) or by cyclizing a reagent of formula (XVIII) with an enamine of formula (XIX).

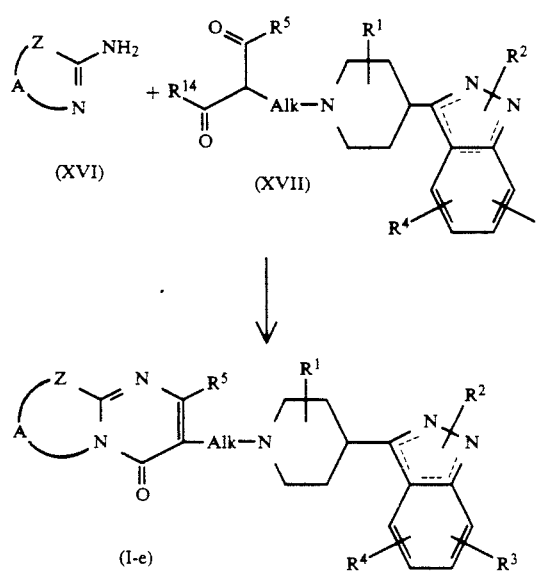

(XVI)  (XVII)

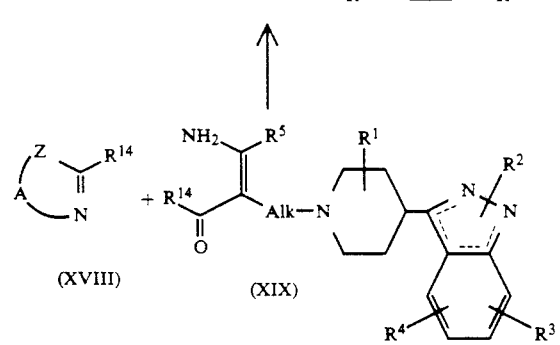

(I-e)

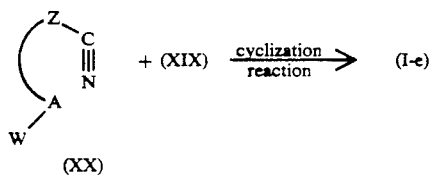

(XVIII)  (XIX)

Said cyclization reactions may generally be carried out by stirring the reactants, optionally in the presence of a suitable reaction-inert solvent such as, for example, an aliphatic, alicyclic or aromatic hydrocarbon, e.g., hexane, cyclohexane, benzene and the like; or pyridine, N,N-dimethylformamide and the like dipolar aprotic solvents. Elevated temperatures may be appropriate to enhance the reaction rate; more in particular it may be advantageous to carry out the reaction at the reflux temperature of the reaction mixture.

Following the same procedure the compounds of formula (I-e) can also be prepared by cyclizing an intermediate of formula (XIX) with a reagent of formula (XX).

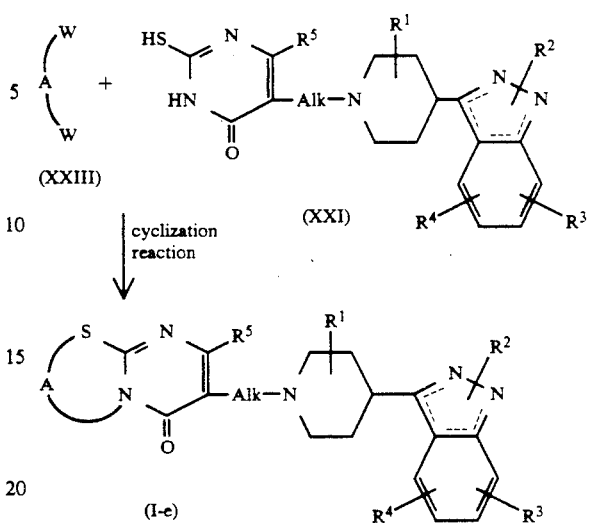

(XX)

The compounds of formula (I-e) wherein Z is S, said compounds being represented by the formula (I-e-1), can also be prepared by cyclizing a 2-mercaptopyrimidinone of formula (XXI) with a reagent of formula (XXII).

(XXIII)  (XXI)

(I-e)

The compounds of formula (I-e-1) wherein A is $CR^8=CR^9$, said compounds being represented by the formula (I-e-2), can be prepared by cyclizing a 2-mercaptopyrimidinone of formula (XXI) with a reagent of formula (XXIII).

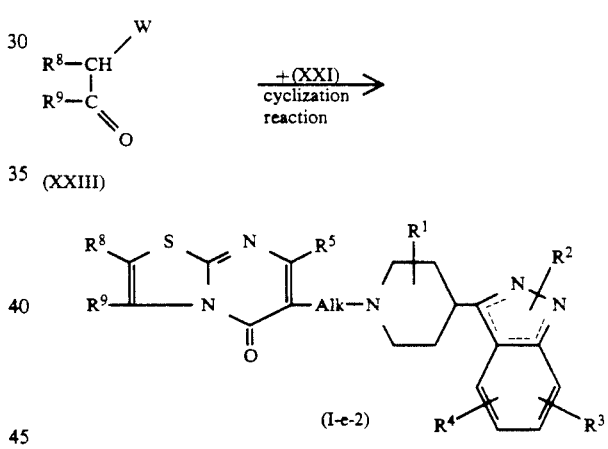

(XXIII)

(I-e-2)

Said cyclization reactions for preparing the compounds of formulae (I-e-1) and (I-e-2) may generally be carried out by stirring the reactants, if desired, in the presence of a suitable reaction-inert solvent such as, for example, an aliphatic, alicyclic or aromatic hydrocarbon, e.g., hexane, cyclohexane, benzene and the like; or pyridine, N,N-dimethylformamide and the like dipolar aprotic solvents. Elevated temperatures may be appropriate to enhance the reaction-rate, more in particular it may be preferred to carry out the reaction at the reflux temperature of the reaction mixture.

The compounds of formula (I) may also be converted into each other following art-known functional group transformation procedures.

For example, the compounds of formula (I-e) and (I-d) wherein $R^{11}$ is amino, maybe derived from the corresponding nitro-substituted quinazolines following art-known nitro-to-amine reduction procedures. A suitable nitro-to-amine reduction procedure is, for example, catalytic hydrogenation in a relatively polar solvent such as, for example, an alcohol, e.g. methanol or ethanol, in the presence of an appropriate catalyst, e.g. platinum-on-charcoal. In some cases it may be useful to add an appropriate catalyst poison such as thiophene to the reaction mixture.

The compounds of formula (I-e) and (I-d) wherein $R^{11}$ is phenylmethoxy may be converted into compounds of formula (I-e) and (I-d) wherein $R^{11}$ is hydroxy following art-known catalytic hydrogenolysis procedures; the compounds of formula (I-e) and (I-d) wherein $R^{11}$ is amino or hydroxy may be converted into compounds of formula (I-e) and (I-d) wherein $R^{11}$ is ($C_{1-10}$alkylcarbonyl)amino and ($C_{1-10}$alkyl-carbonyl)oxy respectively by reacting the former compounds with a suitable acylating agent, e.g. an acyl halide or an acid anhydride; the compounds of formula (I-e) and (I-d) wherein $R^{11}$ is amino may be converted into compounds of formula (I-e) and (I-d) wherein $R^{11}$ is azido by converting the amino group into a diazonium group with nitrous acid or an appropriate alkali metal or earth alkaline metal salt thereof and subsequently converting said diazonium group into an azido group with sodium azide or any other suitable alkali metal or earth alkaline metal azide.

The compounds of formula (I) have basic properties and, consequently, they may be converted to their therapeutically active non-toxic acid addition salt forms by treatment with appropriate acids, such as, for example, inorganic acids, such as hydrohalic acid, e.g. hydrochloric, hydrobromic acid and the like, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butanedioic, (E)-2-butanedioic, 2-hydroxybutanedioic, 2,3-dihydroxybutanedioic, 2-hydroxy-1,2,3-propane-tricarboxylic, methanesulfonic, ethanesulfonic, benzenesulfonic, 4-methyl-benzenesulfonic, cyclohexanesulfamic, 2-hydroxybenzoic, 4-amino-2-hydroxybenzoic and the like acids. Conversely the salt form can be converted into the free base form by treatment with alkali. The term acid addition salt as used hereinabove also comprises the solvates which the compounds of formula (I) are able to form and said solvates are meant to be included within the scope of the present invention. Examples of such solvates are e.g., the hydrates, alcoholates and the like.

A number of intermediates and starting materials in the foregoing preparations are known compounds which may be prepared according to art-known methodologies of preparing said or similar compounds. The intermediates of formula (II) and their preparations are described in U.S. Pat. Nos. 4,335,127, 4,342,870, 4,443,451 and 4,485,107, and in the references cited therein. The intermediates of formula (III) are known from EP-A-0,135,781.

The compounds of formula (I), the pharmaceutically acceptable acid addition salts and stereochemically isomeric forms thereof, are potent antagonists of neurotransmitters and in particular of the mediators serotonin and dopamine. Antagonizing said mediators will suppress or relieve a variety of symptoms associated with phenomena induced by the release, in particular the excessive release, of these mediators. Therapeutic indications for using the present compounds are mainly in the CNS area, the gastrointestinal and cardiovascular field and related domains. Serotonin antagonists are reportedly effective in combatting psychoses, aggressive behaviour, anxiety, depression and migraine. Combined serotonin-dopamine antagonists are especially interesting as they appear to offer relief of both the positive and negative symptoms of schizophrenia. Therapeutic applications in the gastrointestinal field comprise their use as, for instance, antidiarrhoeals, inhibitors of gastro-oesophageal reflux and particularly antiemetics, e.g. in cancer patients receiving chemotherapy and radiation treatment. Further, serotonin is a potent broncho- and vasoconstrictor and thus the present antagonists may be used against hypertension and vascular disorders. In addition, serotonin antagonists have been associated with a number of other properties such as, the suppression of appetite and promotion of weight loss, which may prove effective in combatting obesity; and also the alleviation of withdrawal symptoms in addicts trying to discontinue drinking and smoking habits.

The compounds of the instant invention are particularly useful as antihypertensive agents because of their ability to depress significantly both systolic and diastolic blood pressure in warm-blooded animals. The antihypertensive effect of the instant compounds is evidenced in the "Blood pressure lowering effect in spontaneous hypertensive rats" test. Particularly interesting are also the observations made in the combined "Apomorphine, tryptamine and norepinephrine in rats" test: contrary to most structurally related 3-piperidinyl benzazoles, the instant compounds do not show significant activity on the central nervous system, but rather act peripherally.

In view of their useful pharmacological properties, the subject compounds may be formulated into various pharmaceutical forms for administration purposes. To prepare the pharmaceutical compositions of this invention, an effective amount of the particular compound, in acid addition salt or base form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various way, e.g., as a transdermal patch, as a spot-on or as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutical carrier. Examples of such dosage unit forms are tablets (including scored or coated tablets), capsules, pills, powder packets, wafers, injectable o solutions or suspensions, teaspoonfuls, tablespoon fuls and the like, and segregated multiples thereof.

In view of the usefulness of the subject compounds in the treatment of hypertension it is evident that the present invention provides a method of treating warm-blooded animals suffering from hypertension, said method comprising the systemic administration of a pharmaceutically effective amount of a compound of formula (I) or a pharmaceutically acceptable acid addition salt thereof in admixture with a pharmaceutical carrier. Those of skill in the treatment of hypertension could easily determine the effective amount from the test results presented here. In general it is contemplated that an effective amount would be from 0.01 mg/kg to 4 mg/kg body weight, more preferably from 0.04 mg/kg to 2 mg/kg body weight per day.

It is evident that said effective amount may be lowered or increased depending on the response of the treated subject and/or depending on the evaluation of the physician prescribing the compounds of the instant invention. The effective amount ranges mentioned hereinabove are therefore guidelines only and are not intended to limit the scope or use of the invention to any extent.

The following examples are intended to illustrate and not to limit the scope of the present invention. Unless otherwise stated all parts therein are by weight.

EXPERIMENTAL PART

A. Preparation of Intermediates

EXAMPLE 1 a) To a stirred mixture of 15.8 parts of a sodium hydride dispersion 50% and 660 parts of dimethyl sulfoxide were added portionwise 78.4 parts of 1-acetyl-4-(6-fluoro-2H-indazol-3-yl)piperidine under nitrogen atmosphere. Upon complete addition, stirring was continued for 1 hour at room temperature. 42 Parts of chloromethylbenzene were added dropwise during 45 minutes. Upon completion, stirring was continued overnight at room temperature. The reaction mixture was poured into crushed ice and the product was extracted with dichloromethane. The extract was dried, filtered and evaporated. The residue was purified by column chromatography (HPLC) over silica gel using a mixture of methylbenzene and methanol (90:10 by volume) as eluent. The first fraction was collected and the eluent was evaporated, yielding 91 parts (86.3%) of 1-acetyl-4-[6-fluoro-2-(phenylmethyl)-2H-indazol-3-yl]piperidine as a residue (int. 1).

b) A mixture of 8 parts of 1-acetyl-4-[6-fluoro-2-(phenylmethyl)-2H-indazol-3-yl]-piperidine and 70 parts of a hydrochloric acid solution 6N was stirred for 6 hours at reflux temperature. The reaction mixture was evaporated and the oily residue was crystallized from 2-propanol. The product was filtered off and dried, yielding 2 parts (25.1%) of 6-fluoro-2-(phenylmethyl)-3-(4-piperidinyl)-2H-indazole monohydrochloride; mp. >300° C. (int. 2).

EXAMPLE 2 a) A mixture of 50 parts of 5-methyl-3-isoxazolamine, 70 parts of 3-acetyl-4,5-dihydro-2(3H)-furanone, 435 parts of methylbenzene and 16 parts of polyphosphoric acid was stirred and refluxed for 3 hours using a water separator. The reaction mixture was concentrated in vacuo, yielding 99 parts (95.1%) of 4,5-dihydro-3-[1-(5-methyl-3-isoxazolyl)imino]ethyl]-2(3H)-furanone as an oily residue (int. 3).

b) To a stirred mixture of 98 parts of 4,5-dihydro-3-[1-(5-methyl-3-isoxazolyl)imino]-ethyl]-2-(3H)-furanone, 348 parts of methylbenzene and 300 parts of trichloromethane were added dropwise 150 parts of phosphoryl chloride. Upon complete addition, stirring was continued for 3 hours at reflux temperature. The reaction mixture was concentrated to half its volume and the residue was poured into crushed ice. The whole was treated with an ammonium hydroxide solution and the product was extracted twice with 240 parts of 4-methyl-2-pentanone. The combined extracts were dried, filtered and evaporated in vacuo. The residue was dissolved in trichloromethane, filtered over silica gel and the filtrate was concentrated in vacuo. The residue was crystallized form a mixture of methylbenzene and 2,2'-oxybispropane, yielding 96 parts (88.2%) of 6-(2-chloroethyl)-2,5-dimethyl-7H-isoxazolo[2,3-a]pyrimidin-7-one; mp. 165° C. (int. 4).

B. Preparation of Final Compounds

EXAMPLE 3

A mixture of 4 parts of 3-(2-chloroethyl)-2,4(1H,3H)-quinazolinedione, 4,4 parts of 6-fluoro-1-methyl-3-(1-piperidinyl)-1H-indazole monohydrochloride, 10 parts of sodium carbonate, 0.1 parts of potassium iodide and 144 parts of 4-methyl-2-pentanone was stirred overnight at reflux temperature. After cooling, the reaction mixture was poured into water. The separated organic layer was dried, filtered and evaporated. The residue was purified by column chromatography over silica gel using a mixture of trichloromethane and methanol (95:5 by volume) as eluent. The pure fractions were collected and the eluent was evaporated. The residue was crystallized from acetonitrile. The product was filtered off and dried, yielding 4 parts (59.3%) of 3-[2-[4-(6-fluoro-1-methyl-1H-indazol-3-yl)-1-piperidinyl]ethyl]-2,4(1H,3H)quinazolinedione; mp. 250.1° C. (compound 1).

EXAMPLE 4

A mixture of 4.4 parts of 6-(2-bromoethyl)-2,3-dihydro-7-methyl-5H-thiazolo[3,2-a]pyrimidin-5-one monohydrobromide, 3.7 parts of 6-fluoro-3-(4-piperidinyl)-1H-indazole dihydrochloride, 4.25 parts of sodium carbonate and 120 parts of 4-methyl-2-pentanone was stirred for 6 hours at reflux temperature. After cooling, the reaction mixture was filtered, The precipitate was stirred in water and the whole was filtered again. The precipitated product was purified by column chromatography over silica gel using a mixture of trichloromethane and methanol (90:10 by volume) as eluent. The pure fractions were collected and the eluent was evaporated. The residue was crystallized from 2-propanol. The product was filtered off and dried, yielding 2.5 parts (48.3%) of 6-[2-[4-(6-fluoro-1H-indazol-3-yl)-1-piperidinyl]ethyl]-2,3-dihydro-7-methyl-5H-thiazolo[3,2-a]pyrimidin-5-one; mp. 207.6° C. (compound 2).

EXAMPLE 5

0.7 Parts of a sodium hydride dispersion 50% in mineral oil were suspended in petroleum ether under a nitrogen atmosphere. The solvent was decanted and 55 parts of dimethyl sulfoxide were added. 6 Parts of 6-[2-[4-(6-fluoro-1H-indazol-3-yl)-1-piperidinyl]ethyl]-2,3-dihydro-7-methyl-5H-thiazolo[3,2-a]pyrimidin-5-one were added portionwise while stirring at room temperature. Upon complete addition, stirring was continued for 1 hour at room temperature. After the dropwise addition of 2.6 parts of 1-chloromethyl-4-methoxybenzene, the reaction mixture was stirred overnight at room temperature. The whole was poured into water and the product was extracted with dichloromethane. The extract was dried, filtered and evaporated. The residue was purified by column chromatography (silica gel; CHCl$_3$/CH$_3$OH 95:5). The eluent of the desired fraction was evaporated and the residue was crystallized from 2-propanol. The product was filtered off and dried, yielding 2.4 parts (30.0%) of 6-[2-[4-[6-fluoro-1-[(4-methoxyphenyl)methyl]-1H-indazol-3-yl]-1-piperidinyl]ethyl]-2,3-dihydro-7methyl-5H-thiazolo[3,2-a]pyrimidin-5-one; mp. 145.8° C. (compound 30).

EXAMPLE 6

A mixture of 3.2 parts of 3-[2-[4-(6-fluoro-1H-indazol-3-yl)-1-piperidinyl]ethyl]-2,9-dimethyl-4H-pyrido[1,2-a]pyrimidin-4-one, 27 parts of acetic anhydride and 15.7 parts of acetic acid was stirred for 2 hours at reflux temperature. The reaction mixture was evaporated and the residue was poured into 100 parts of water. After basifying with NH$_4$OH, the product was extracted with dichloromethane. The extract was dried, filtered and evaporated and the residue was crystallized from 2-propanol, yielding 3.3 parts (95.3%) of 3-[2-[4-(1-acetyl-6-fluoro-1H-indazol-3-yl)-1-piperidinyl]ethyl]-2,9-dimethyl-4H-pyrido[1,2-a]pyrimidin-4-one; mp. 210.3° C. (compound 46). All other compounds listed in tables 1 to 3 were obtained following methods of preparation analogous to those described in examples 2 to 6, as is indicated in the column headed by Ex. No.

TABLE 1

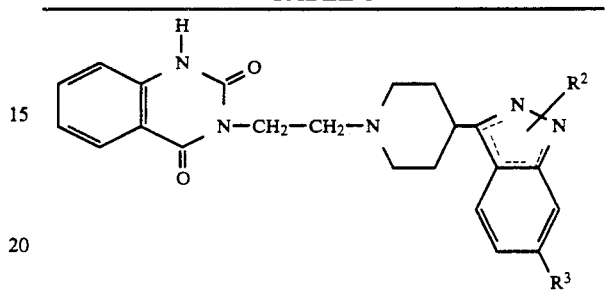

| Comp. No. | Ex. No. | R$^2$ | R$^3$ | Physical Data |
|---|---|---|---|---|
| 3 | 3 | 4-F—C$_6$H$_4$ | F | HCl/mp. 291.5° C. |
| 4 | 3 | H | F | mp. 278.9° C. |
| 5 | 3 | CH$_2$—C$_6$H$_5$ | F | mp. 223.5° C. |
| 53 | 3 | H | OCH$_3$ | 2 HCl/H$_2$O/mp. 244.3° C. |

TABLE 2

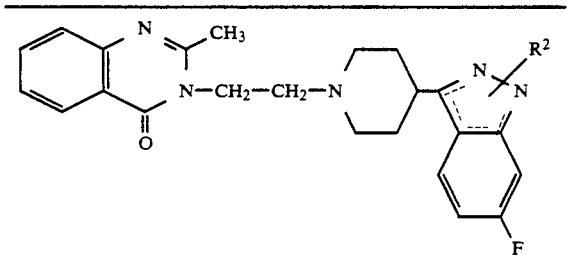

| Comp. No. | Ex. No. | R$^2$ | Physical Data |
|---|---|---|---|
| 6 | 4 | H | mp. 259.7° C. |
| 7 | 3 | CH$_3$ | mp. 143.8° C. |
| 8 | 3 | CH$_2$—C$_6$H$_5$ | mp. 98.3° C. |

TABLE 3

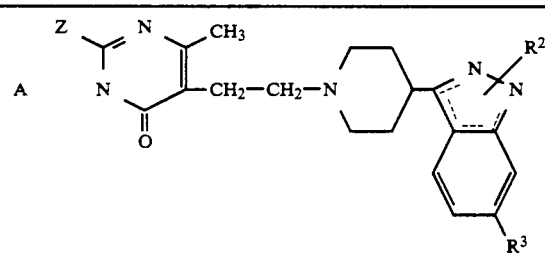

| Comp. No. | Ex. No. | —Z—A— | R$^2$ | R$^3$ | Physical Data |
|---|---|---|---|---|---|
| 9 | 3 | —CH=CH—CH=CH— | 4-F—C$_6$H$_4$ | F | mp. 147.5° C. |
| 10 | 3 | —CH=CH—CH=CH— | H | F | mp. 259.5° C. |
| 11 | 3 | —CH=CH—CH=CH— | CH$_3$ | F | mp. 149.8° C. |
| 12 | 3 | —CH=CH—CH=CH— | CH$_2$—C$_6$H$_5$ | F | mp. 131.4° C. |
| 13 | 3 | —(CH$_2$)$_4$— | H | F | mp. 236.2° C. |
| 14 | 3 | —(CH$_2$)$_4$— | CH$_3$ | F | mp. 168.1° C. |
| 15 | 3 | —(CH$_2$)$_4$— | CH$_2$—C$_6$H$_5$ | F | mp. 162.1° C. |
| 16 | 3 | —S—CH=CH— | 4-F—C$_6$H$_4$ | F | (E)-2-butenedioate/ mp. 232.4° C. |

TABLE 3-continued

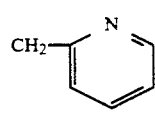

| Comp. No. | Ex. No. | —Z—A— | R² | R³ | Physical Data |
|---|---|---|---|---|---|
| 17 | 3 | —S—CH=CH— | H | F | ½ H₂O/mp. 190.1° C. |
| 18 | 3 | —S—CH=CH— | CH₃ | F | mp. 139.9° C. |
| 19 | 3 | —S—CH=CH— | CH₂—C₆H₅ | F | mp. 127.6° C. |
| 20 | 4 | —S—CH=C(CH₃)— | 4-F—C₆H₄ | F | ½ (E)-2-butenedioate/ H₂O/mp. 165.0° C. |
| 21 | 3 | —S—CH=C(CH₃)— | CH₃ | F | mp. 170.0° C. |
| 22 | 4 | —S—CH=C(CH₃)— | H | F | mp. 232.4° C. |
| 23 | 3 | —S—CH=C(CH₃)— | CH₂—C₆H₅ | F | mp. 141.1° C. |
| 24 | 3 | —S—CH=C(CH₃)— | 2-CH₂—C₆H₅ | F | mp. 180.0° C. |
| 25 | 3 | —S—(CH₂)₂— | CH₃ | F | mp. 157.6° C. |
| 26 | 3 | —S—(CH₂)₂— | CH₂—C₆H₅ | F | mp. 150.2° C. |
| 27 | 3 | —S—(CH₂)₂— | 2-CH₂—C₆H₅ | F | mp. 175.2° C. |
| 28 | 3 | —C(CH₃)=CH—CH=CH— | H | F | mp. 213.1° C. |
| 29 | 3 | —C(CH₃)=CH—CH=CH— | CH₂C₆H₅ | F | mp. 139° C. |
| 30 | 5 | —S—(CH₂)₂— | CH₂-(4-OCH₃C₆H₄) | F | mp. 145.8° C. |
| 31 | 3 | —CH=C(CH₃)—O— | CH₂—C₆H₅ | F | mp. 136.1° C. |
| 32 | 4 | —S—CH=C(CH₃)— | CH₂-(4-F—C₆H₄) | F | mp. 139.2° C. |
| 33 | 3 | —C(CH₃)=CH—CH=CH— | H | OCH₃ | mp. 210.0° C. |
| 34 | 3 | —S—CH=CH— | H | OCH₃ | mp. 183.2° C. |
| 35 | 3 | —S—CH=CH— | H | H | 2 HCl/mp. 196.4° C. |
| 36 | 5 | —(CH₂)₄— | CH₂—(2-pyridyl) | F | (E)-2-butenedioate(1:1) mp. 151.2° C. |
| 37 | 3 | —C(CH₃)=CH—CH=CH— | —CH₂CH₂OH | F | mp. 176.0° C. |
| 38 | 3 | —(CH₂)₄— | —CH₂CH₂OH | F | mp. 140.1° C. |
| 39 | 3 | —S—(CH₂)₂— | —CH₂CH₂OH | F | mp. 165.6° C. |
| 40 | 3 | —C(CH₃)=CH—CH=CH— | H | H | mp. 180.2° C. |
| 41 | 3 | —CH=C(CH₃)—O— | CH₃ | F | mp. 157.7° C. |
| 42 | 3 | —(CH₂)₄— | H | H | mp. 188.1° C. |
| 43 | 3 | —S—CH=CH— | —CH₂CH₂OH | F | mp. 197.2° C. |
| 44 | 5 | —(CH₂)₄— | CH₂—(2-furyl) | F | mp. 179.4° C. |
| 45 | 3 | —S—CH₂—CH₂ | H | H | mp. 210.3° C. |
| 46 | 6 | —C(CH₃)=CH—CH=CH— | COCH₃ | F | |
| 47 | 6 | —C(CH₃)=CH—CH=CH— | CO(4-Cl—C₆H₅) | F | mp. 181.6° C. |
| 48 | 6 | —C(CH₃)=CH—CH=CH— | COOC₂H₅ | F | mp. 183.1° C. |
| 49 | 3 | —S—CH₂—CH₂— | H | H | |
| 50 | 6 | —C(CH₃)=CH—CH=CH— | COCH₃ | H | mp. 160.7° C. |
| 51 | 6 | —(CH₂)₄— | COCH₃ | H | mp. 149.3° C. |
| 52 | 3 | —S—CH₂—CH₂— | COCH₃ | H | |

C) Pharmacological Examples

The activity of the subject compounds as antagonists of neurotransmitters is evidenced by the experimental data obtained in at least one of two different test procedures, viz., the combined apomorphine-, tryptamine- and norepinephrine tests in rats and the apomorphine test in dogs. The tests are carried out following the procedures described hereafter and the experimental data are summarized in table 4. The antihypertensive effect of the instant compounds is evidenced by the "Blood pressure lowering effect in spontaneous hypertensive rats" test. The experimental data are summarized in table 5.

EXAMPLE 7

The Combined Apomorphine (APO)-, Tryptamine (TRY)- and Norepinephrine (NOR) Test in Rats The experimental animals used in this test were adult male Wistar rats (weight 240±10 g). After an overnight fast, the animals were treated subcutaneously or orally with an aqueous solution of the compound under investigation (1 ml/100 g body weight) (time=zero) and put in isolated observation cages. Thirty minutes thereafter (time=30 minutes) 1.25 mg/kg of apomorphine hydrochloride (APO) was injected intravenously and the rats were observed over a 1 hour period for the presence or absence of the following apomorphine-induced phenomena: agitation and stereotypic chewing. At the end of this 1 hour period (time=90 minutes) the same animals were injected intravenously with 40 mg/kg of tryptamine (TRY) and the presence of the typical tryptamine-induced bilateral tonic seizures and hyperaemia of the ears was noted. Two hours after pretreatment (time=120 minutes) finally, the same animals were challenged with 1.25 mg/kg intravenously of norephinephrine (NOR) and possible mortality was looked for up to 60 minutes later.

The table 4 gives the ED$_{50}$-values of a number of the compounds under consideration. As used herein, the ED$_{50}$-value represents the dose which protects 50% of the animals from apomorphine-, tryptamine- or norepinephrine-induced phenomena.

The Apomorphine Test in Dogs (APO-Dog)

The method used is described by P. A. J. Janssen and C. J. E. Niemegeers in Arzneim.-Forsch. (Drug Res.), 9, 765-767 (1959). The compounds listed in table 4 were administered subcutaneously or orally to beagle dogs at different doses and the animals were challenged one hour thereafter with a standard dose of 0.31 mg/kg (s.c.) of apomorphine.

The table 4 gives the ED$_{50}$-values of a number of the compounds under consideration. As used herein, the ED$_{50}$ value represents the dose which protects 50% of the animals from emesis.

The compounds listed in table 4 are not given for the purpose of limiting the invention thereto but only to exemplify the useful pharmacological activities of all the compounds within the scope of formula (I).

TABLE 4

| | Combined test in rats; ED$_{50}$ in mg/kg | | | | |
|---|---|---|---|---|---|
| Comp. No. | (APO) | (TRY)-convulsions | (TRY)-hyperaemia | (NOR) | (APO)-dog test, ED$_{50}$ in mg/kg |
| 2 | 5 | 5 | 0.005 | 0.31 | 0.002 |
| 9 | >10 | 5 | 0.08 | 5 | |
| 11 | 5 | 0.31 | 0.005 | 0.08 | 0.12 |
| 13 | >10 | 1.25 | 0.02 | 0.31 | 0.015 |
| 16 | >10 | 5 | 0.08 | >10 | |
| 17 | 5 | 5 | 0.03 | 2.0 | 0.004 |
| 18 | 5 | 1.25 | 0.005 | 1.25 | 0.2 |
| 20 | >10 | ≧10 | 0.08 | >10 | |
| 21 | 1.25 | 0.08 | 0.005 | 0.31 | 0.12 |
| 25 | >10 | 1.25 | 0.01 | 0.31 | <0.015 |
| 29 | 1.25 | 5 | ≦0.16 | 1.25 | 0.004 |
| 30 | >10 | 10 | 0.08 | 5 | >0.63 |
| 31 | >10 | 1.25 | 0.02 | 0.31 | >0.63 |
| 34 | >10 | >10 | 1.25 | 1.25 | >0.01 |

EXAMPLE 8

Blood pressure lowering effect in spontaneous hypertensive rats (SHR)

Adult spontaneous hypertensive rats (6 months of age) were anesthetized by ether inhalation. The femoral artery was dissected and cannulated, and the catheter was connected to a strain-gauge blood pressure transducer. When the animals were fully awake, they were restrained and the systolic and diastolic arterial blood pressure were continuously recorded. An observation period of at least 30 min. preceded the administration of the test compound. All test compounds were dissolved in 20% polypropylene glycol and injected intraperitoneally. After administration of the test drug the systolic and diastolic arterial blood pressure and the heart rate were recorded during a period of 120 minutes. The average blood pressure and heart rate was calculated from the results obtained at various time intervals after administration of the test drug. The following table illustrates the lowering of the systolic and diastolic blood pressure.

| Comp. No. | SBP (mm Hg) | DBP (mm Hg) |
|---|---|---|
| 2 | −140 | −100 |
| 9 | −40 | −30 |
| 11 | −130 | −90 |
| 13 | −120 | −80 |
| 18 | −90 | −70 |
| 25 | −170 | −90 |
| 28 | −140 | −100 |
| 29 | −30 | −30 |
| 30 | −70 | −55 |
| 31 | −80 | −60 |
| 34 | −20 | −10 |
| 46 | −100 | −65 |
| 47 | −90 | −60 |
| 48 | −110 | −85 |
| 53 | −60 | −45 |

D) Composition Examples

EXAMPLE 9: ORAL DROPS

500 Parts of the A.I. was dissolved in 0.5 l of 2-hydroxypropanoic acid and 1.5 l of the polyethylene glycol at 60°-80° C. After 30°-40° C. there were added 35 l of polyethylene glycol and the mixture was stirred well. Then there was added a solution of 1750 parts of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

EXAMPLE 10: ORAL SOLUTION

9 Parts of methyl 4-hydroxybenzoate and 1 part of propyl 4-hydroxybenzoate were dissolved in 4 l of boiling purified water. In 3 l of this solution were dissolved first 10 parts of 2,3-dihydroxybutanedioic acid and thereafter 20 parts of the A.I. The latter solution was combined with the remaining part of the former solution and 12 l 1,2,3-propanetriol and 3 l of sorbitol 70% solution were added thereto. 40 Parts of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE 11: CAPSULES

20 Parts of the A.I., 6 parts sodium lauryl sulfate, 56 parts starch, 56 parts lactose, 0.8 parts colloidal silicon dioxide, and 1.2 parts magnesium stearate were vigorously stirred together. The resulting mixture was subsequently filled into 1000 suitable hardened gelatin capsules, comprising each 20 mg of the active ingredient.

EXAMPLE 12: FILM-COATED TABLETS

Preparation of Tablet Core

A mixture of 100 parts of the A.I., 570 parts lactose and 200 parts starch was mixed well and thereafter humidified with a solution of 5 parts sodium dodecyl sulfate and 10 parts polyvinylpyrrolidone (Kollidon-K 90 ®)) in about 200 ml of water. The wet powder mixture was sieved, dried and sieved again. Then there was added 100 parts microcrystalline cellulose (Avicel ®)) and 15 parts hydrogenated vegetable oil (Sterotex ®)). The whole was mixed well and compressed into tablets, giving 10,000 tablets, each containing 10 mg of the active ingredient.

Coating

To a solution of 10 parts methyl cellulose (Methocel 60 HG ®)) in 75 ml of denaturated ethanol there was added a solution of 5 parts of ethyl cellulose (Ethocel 22 cps ®)) in 150 ml of dichloromethane. Then there were added 75 ml of dichloromethane and 2.5 ml 1,2,3-propanetriol. 10 Parts of polyethylene glycol was molten and dissolved in 75 ml of dichloromethane. The latter solution was added to the former and then there were added 2.5 parts of magnesium octadecanoate, 5 parts of polyvinylpyrrolidone and 30 ml of concentrated colour suspension (Opaspray K-1-2109 ®)) and the whole was homogenated. The tablet cores were coated with the thus obtained mixture in a coating apparatus.

EXAMPLE 13: INJECTABLE SOLUTION 1.8 Parts methyl 4-hydroxybenzoate and 0.2 parts propyl 4-hydroxybenzoate were dissolved in about 0.5 l of boiling water for injection. After cooling to about 50° C. there were added while stirring 4 parts lactic acid, 0.05 parts propylene glycol and 4 parts of the A.I. The solution was cooled to room temperature and supplemented with water for injection q.s. ad 1 l, giving a solution comprising 4 mg/ml of A.I. The solution was sterilized by filtration (U.S.P. XVII p. 811) and filled in sterile containers.

EXAMPLE 14: SUPPOSITORIES

3 Parts A.I. was dissolved in a solution of 3 parts 2,3-dihydroxybutanedioic acid in 25 ml polyethylene glycol 400. 12 Parts surfactant (SPAN ®)) and triglycerides (Witepsol 555 ®)) q.s. ad 300 parts were molten together. The latter mixture was mixed well with the former solution. The thus obtained mixture was poured into moulds at a temperature of 37°–38° C. to form 100 suppositories each containing 30 mg/ml of the A.I..

We claim:

1. A chemical compound having the formula

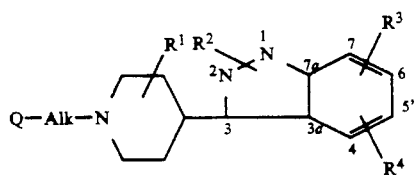

(I)

a pharmaceutically acceptable acid addition salt or a stereochemically isomeric form thereof, wherein $R^1$ is hydrogen or $C_{1-6}$alkyl;

$R^2$ is hydrogen; $C_{1-6}$alkyl; hydroxy$C_{1-6}$alkyl; phenyl optionally substituted with up to three substituents independently selected from $C_{1-6}$alkyl, $C_{1-6}$alkyloxy, hydroxy, halo, amino, nitro and trifluoromethyl; aryl$C_{1-6}$alkyl; $C_{1-6}$alkylcarbonyl; $C_{1-6}$alkyloxycarbonyl or phenylcarbonyl, wherein phenyl is optionally substituted with up to three substituents independently selected from $C_{1-6}$alkyl, $C_{1-}$ $_6$alkyloxy, hydroxy, halo, amino, nitro and trifluoromethyl;

$R^3$ and $R^4$ each independently are hydrogen, halo, hydroxy, $C_{1-6}$alkyloxy or $C_{1-6}$alkyl;

Alk is $C_{1-4}$alkanediyl; and

Q is a bicyclic heterocyclic radical of formula

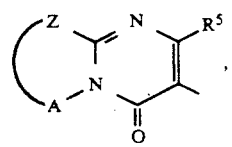

(a)

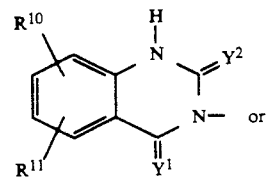

(b)

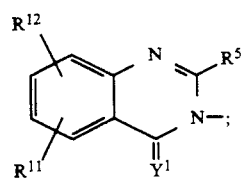

(c)

wherein $R^5$ is hydrogen or $C_{1-6}$alkyl;

Z is —S— or —$CR^6$=$CR^7$—; said $R^6$ and $R^7$ each independently being hydrogen or $C_{1-6}$alkyl; or Z is —$CH_2$— wherein one hydrogen atom may be replaced by hydroxy or $C_{1-6}$alkyl;

A is a bivalent radical —$CH_2$—$CH_2$— or —$CH_2$—$CH_2$—$CH_2$— wherein in the latter two radicals one or two hydrogen atoms may be replaced by $C_{1-6}$alkyl; or A is a bivalent radical —$CR^8$=$CR^9$, wherein $R^8$ and $R^9$ each independently are hydrogen, halo, amino or $C_{1-6}$alkyl; or when Z is —S—, then A may also be —$CR^{10}$=N—, $R^{10}$ being hydrogen or $C_{1-6}$alkyl; or when Z is —$CR^6$=$CR^7$—, then A also may be —O—; and $Y^1$ and $Y^2$ each independently are O and S;

$R^{11}$ is hydrogen, halo, $C_{1-6}$alkyl, $C_{1-6}$alkyloxy, trifluoromethyl, nitro, amino, mono- or di($C_{1-6}$alkyl)amino, $C_{1-10}$aklylcarbonylamino, cyano, hydroxy, $C_{1-10}$alkylcarbonyloxy, phenylmethoxy or azido;

$R^{12}$ is hydrogen or halo; and aryl is phenyl optionally substituted with up to three substituents independently selected from $C_{1-6}$alkyl, $C_{1-6}$alkyloxy, hydroxy, halo, amino, nitro and trifluoromethyl; pyridinyl, furanyl or $C_{1-6}$alkyl substituted furanyl.

2. A chemical compound according to claim 1 wherein $R^1$ is hydrogen; $R^2$ is substituted on $N^1$, $R^3$ and $R^4$ each independently are hydrogen, $C_{1-6}$alkyloxy or halo; Q is a radical of formula (a) wherein $R^5$ is $C_{1-6}$alkyl.

3. A chemical compound according to claim 1 wherein $R^2$ is hydrogen, $C_{1-6}$alkyl, phenyl optionally substituted with halo or trifluoromethyl, or phenylmethyl optionally substituted with halo, $C_{1-6}$alkyloxy or trifluoromethyl; $R^3$ is halo; $R^4$ is hydrogen.

4. A chemical compound according to claim 1 wherein $R^3$ is 6-fluoro.

5. An antihypertensive composition comprising one or more inert carriers and as active ingredient an antihypertensively effective amount of a chemical compound as claimed in any of claims 1 to 4.

6. The compound of claim 1 wherein said compound is selected from the group consisting of:

6-[2-[4-(6-fluoro-1H-indazol-3-yl)-1-piperidinyl]ethyl]-2,3-dihydro-7-methyl-5 H-thiazolo[3,2-a]pyrimidin-5-one;

3-[2-[4-(6-fluoro-1-methyl-1H-indazol-3-yl)-1-piperidinyl]-ethyl]-2-methyl-4H-pyrido[1,2-a]pyrimidin-4-one;

3-[2-[4-(6fluoro-1H-indazol-3-yl)-1-piperidinyl]ethyl]-6,7,8,9-tetrahydro-2-methyl-4H-pyrido[1,2,-a]pyrimidin-4-one;

6-[2-[4-(6-fluoro-1-methyl-1H-idazol-3-yl)-1-piperidinyl]-ethyl]-2,3-dihydro-7-methyl-5H-thiazolo[3,2-a]pyrimidin-5-one;

3-[2-[4-(6-fluor-1H-indazol-3-yl)-1-piperidinyl]ethyl]-2,9-d imethyl-4H-pyrido[1,2-a]pyrimidin-4-one;

3-[2-[4-(1-acetyl-6-fluoro-1H-indazol-3-yl)-1-piperidinyl]-ethyl]-2,9-dimethyl-4H-pyrido[1,2-a]pyrimidin-4-one; and ethyl 3-[1-[2-(2,9-dimethyl-4-oxo-4H-pyrido[1,2-a]pyrimidin-3-yl)ethyl]-4-piperidinyl]-6-fluoro-1H-indazole-1-carboxylate. 4

* * * * *

UNITED STATES PATENT AND TRADEMARK OFFICE
CERTIFICATE OF CORRECTION

PATENT NO. : 5,196,425    Page 1 of 2

DATED : March 23, 1993

INVENTOR(S) : Jan Vandenberk, Beerse; Ludo E. J. Kennis, Turnhout; Albertus H. M. T. Van Heertum, Beerse It is certified that error appears in the above-identified patent and that said Letters Patent is hereby corrected as shown below:

In Column 1, between lines 25 and 35, Formula (I) should appear as follows:

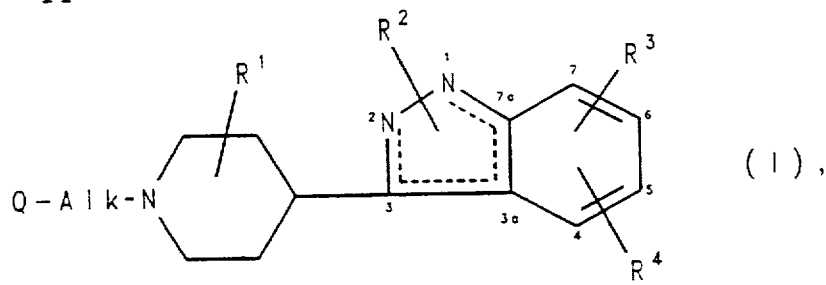

and in Column 21, between lines 50 and 57, Formula (I) should appear as follows:

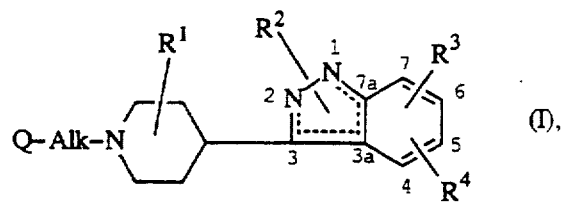

UNITED STATES PATENT AND TRADEMARK OFFICE
CERTIFICATE OF CORRECTION

PATENT NO. : 5,196,425
DATED : March 23, 1993
INVENTOR(S) : Jan Vandenberk, et al It is certified that error appears in the above-indentified patent and that said Letters Patent is hereby corrected as shown below:

In both places in the printed patent where Formula (I) appears, the optional double bond (shown as dotted lines) in the five-membered ring, are not shown.

Signed and Sealed this

Sixteenth Day of August, 1994

*Attest:*

BRUCE LEHMAN

*Attesting Officer*     *Commissioner of Patents and Trademarks*